(12) United States Patent
Langford et al.

(10) Patent No.: US 8,691,213 B2
(45) Date of Patent: Apr. 8, 2014

(54) PROTEIN FREE FORMULA

(75) Inventors: Jane Elizabeth Langford, Liverpool (GB); Ian Sullivan, Wirral (GB); Catherine Teresa Deering, Liverpool (GB); Sandra Helen Giffen, Liverpool (GB)

(73) Assignee: SHS International, Liverpool (GB)

( * ) Notice: Subject to any disclaimer, the term of this patent is extended or adjusted under 35 U.S.C. 154(b) by 1106 days.

(21) Appl. No.: 12/666,845

(22) PCT Filed: Jul. 5, 2007

(86) PCT No.: PCT/GB2007/002520
§ 371 (c)(1),
(2), (4) Date: Dec. 28, 2009

(87) PCT Pub. No.: WO2008/015374
PCT Pub. Date: Feb. 7, 2008

(65) Prior Publication Data
US 2010/0172876 A1 Jul. 8, 2010

Related U.S. Application Data

(60) Provisional application No. 60/821,461, filed on Aug. 4, 2006.

(51) Int. Cl.
*A01N 63/00* (2006.01)
*A61K 38/46* (2006.01)
*A61K 38/47* (2006.01)
*A61K 38/48* (2006.01)
*A61K 35/20* (2006.01)
*A61K 31/70* (2006.01)
*A23J 1/20* (2006.01)

(52) U.S. Cl.
USPC ... 424/93.4; 424/94.6; 424/94.61; 424/94.63; 424/535; 514/23; 426/656

(58) Field of Classification Search
None
See application file for complete search history.

(56) References Cited

U.S. PATENT DOCUMENTS

| 6,077,558 | A | 6/2000 | Euber |
| 2002/0106436 | A1 | 8/2002 | Gohman |

FOREIGN PATENT DOCUMENTS

| DE | 10221403 A1 | 12/2003 |
| EP | 1597978 | 11/2005 |
| EP | 1714660 | 10/2006 |
| EP | 1714660 A1 * | 10/2006 |
| EP | 1852498 | 11/2007 |
| RU | 2282995 | 5/2006 |
| WO | WO 2005/039319 | 5/2005 |
| WO | WO 2006/073145 | 7/2006 |
| WO | WO 2006/091103 | 8/2006 |
| WO | WO 2007/054969 | 5/2007 |

OTHER PUBLICATIONS

Saulnier, D.M.; Kolida, S.; Gibson, G.R. "Microbiology of the Human Intestinal Tract and Approaches for its Dietary Modulation" Current Pharmaceutical Design, 2009, 15(13), pp. 1403-1414.*
Prioult, Guénolée; Pecquet, Sophie ; Fliss, Ismail "Allergenicity of Acidic Peptides from Bovine β-Lactoglobulin is Reduced by Hydrolysis with *Bifidobacterium lactis* NCC362 Enzymes" Intl. Dairy J., May 2005, 15(5), pp. 439-448.*
Hol, J et al "The acquisition of tolerance toward cow's milk through probiotic supplementation: A randomized, controlled trial" J Allergy Clin Immunol, 2008,121(6), pp. 1448-1454.*
Ohira, Iichiroh "Probiotics 12 Plus" <URL:www.holisticahealingspa.com/ohhiras.htm>, archived online Apr. 27, 2005, 4 pages.*
Bunselmeyer, Probiotics and prebiotics for the prevention and treatment of atopic eczema, Der Hautarzt; Zeitschrift fur dermatologie, Venerologie und Verwandte Gebiete, Springer-Verlag, BE, vol. 57, No. 9, Oct. 21, 2005, pp. 785-791, XP019393123 online, ISSN 1432-1173, p. 790, col. 2, paragraph 2.
International Search Report for WO 2008/015374 dated Feb. 13, 2008, 4 pages.
Moro et al., A mixture of prebiotic oligosaccharides reduces the incidence of atopic dermatitis during the first six months of age, Arch. Dis. Child, vol. 91, Jul. 27, 2006, pp. 814-819, XP002468866, p. 814, table 3, figure 2.
Written Opinion re WO 2008/015374 dated Feb. 13, 2008, 9 pages.

* cited by examiner

*Primary Examiner* — Chris R Tate
*Assistant Examiner* — Aaron J Kosar
(74) *Attorney, Agent, or Firm* — Woodard, Emhardt, Moriarty, McNett & Henry LLP

(57) ABSTRACT

The invention relates to the use of composition comprising free amino acids as a sole source of protein, a fatty acid source comprising long chain polyunsaturated fatty acids, a carbohydrate source comprising digestible and indigestible carbohydrates, and milk protein free Bifidobacteria for treating a person suffering from (a) colic, congestion, runny nose, wheezing, vomiting, diarrhea, bloody stools, mucus in stools, rash, eczema, gastroesophageal reflux, eosinophilic esophagitis or asthma; (b) cow's milk allergy and/or food protein intolerance; and/or (c) infections, wherein the indigestible carbohydrate is selected from a milk protein free source and the total composition is essentially free of intact proteins.

10 Claims, 2 Drawing Sheets

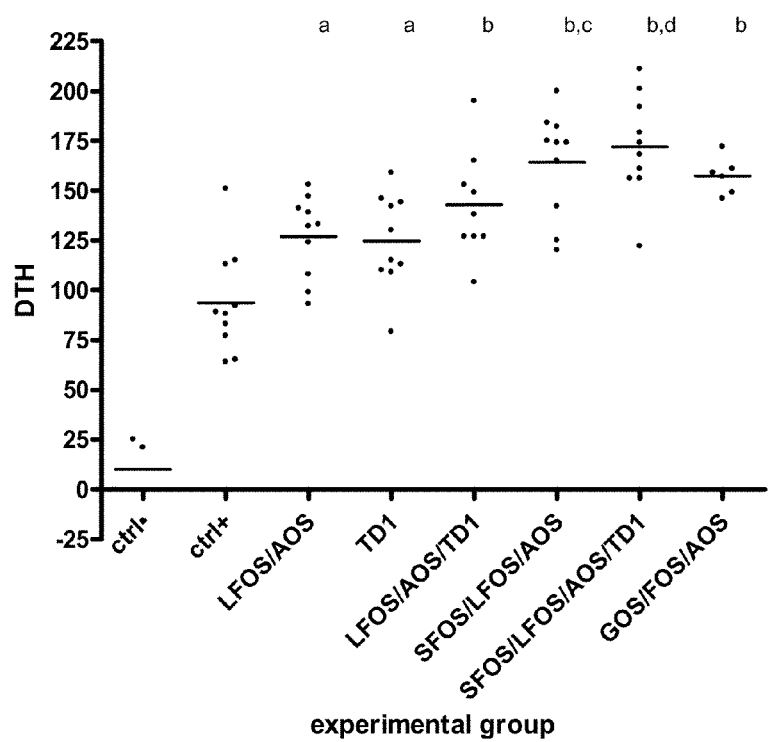
Figure 1- Mouse Vaccine Model
a= p<0.05 compared to ctrl+, b= p<0.01 compared to ctrl+, c= p<0.05 compared to LFOS/AOS, d= p<0.001 compared to TD1(=*Bifidobacterium breve*).

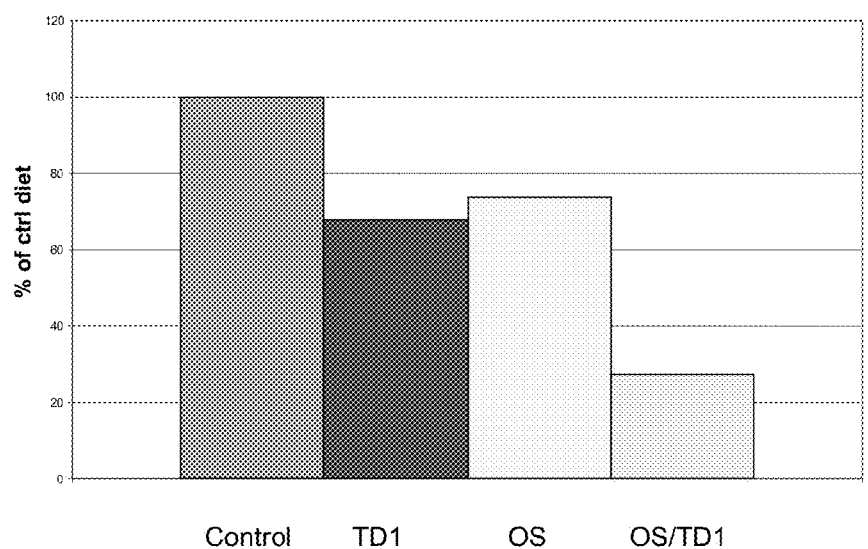
Fig. 2- Mouse Casein Allergy Model

PROTEIN FREE FORMULA

This application is a national stage of PCT/GB2007/002520 filed Jul. 5, 2007, which claims the benefit of U.S. Provisional Application Ser. No. 60/821,461 filed Aug. 4, 2006.

FIELD OF THE INVENTION

The present invention relates to the stimulation of health in infants receiving an amino acid based formula.

BACKGROUND OF THE INVENTION

In a preferred situation, infants are breastfed by the mother. However, often in infants, after an initial period of being breast fed, breastfeeding is stopped and the infant diet comprises mainly infant milk formula.

However in a small group of infants breastfeeding or the feeding of conventional infant formula results in adverse reactions, such as pain and allergic reaction. People suffering from an allergy may have difficulties in digesting or metabolizing some food constituents, which then lead to gastrointestinal and systemic allergic reactions. The allergic reactions are mainly directed to the protein fraction in the food. A significant change in the diet is often necessary to reduce adverse events.

To prevent allergic reactions to protein, the infant food consists of hydrolysed milk proteins, amino acids or non-milk proteins e.g. soy proteins and other nutritional components which do not cause allergic reactions.

A known infant nutrition comprising amino acids as the nitrogen source is Neocate™ for use in patients suffering from allergy, gastro-intestinal complaints, eczema, malabsorption or maldigestion.

In the prior art the number of different sources of nutrients is often kept low to prevent introducing allergens in the formula by the addition of these ingredients. However, this has the disadvantage that infant also do not benefit from the beneficial effects of such additional ingredients.

WO2005039319 discloses the use of synbiotics in infant formula including protein in hydrolysate form, thereby reducing the risk of allergy (page 11, line 35-37)

WO2006091103 discloses a nutritional composition comprising synbiotics for the treatment and prevention of immune disorders including allergy. The use of protein hydrolysate and/or free amino acids for reducing the risk of allergy is disclosed.

It is the aim of the present invention to improve the dietary formulas for this vulnerable patient group by providing additional nutritional benefits without introducing allergens in the composition.

SUMMARY OF THE INVENTION

The present inventors have recognized that in an elemental formula containing a variety of free amino acids without intact protein, it is highly unpredictable how the intestinal flora develops. Instead of the bifidobacteria and lactobacilli dominant flora in normal infants receiving breast milk, many other bacterial species, including potentially pathogenic species, may prevail in the intestine of infants receiving amino acid based foods.

The development of a healthy intestinal flora is particularly important in all infants, as these infants often already suffer from an impaired immunological function, resulting in colic, congestion, runny nose, wheezing, vomiting, diarrhea, bloody stools, mucus in stools, rash, or eczema.

The present inventors have recognized that the healthy flora development is of very high importance in infants receiving a diet containing mainly free amino acid as a protein source. Without being bound by theory, the inventors recognized that a good flora, i.e. a flora rich in Bifidobacteria and Lactobacilli, is especially beneficial for the maturation of the (mucosal) immune system. A good flora prevents the development of allergies or at least reduces the severity of the allergies in such infants. Hence the present inventors recognized the criticality of a beneficial flora development in these infants.

In spite of the limitations in formulation of the dietary formula for such vulnerable infants, the present inventors found that a specific selection of dietary oligosaccharides, preferably fructans and/or pectin degradation products can be beneficially added to the elemental formula to stimulate the flora development without causing any allergic side effects.

No milk derived products can be used in this elemental formula, since this might lead to the addition of milk allergens to the product. Therefore the prebiotic fibres according to this invention are carefully selected from the known prebiotic fibres in order to prevent the addition of milk or other intact and potential allergenic proteins that are present in the fibres to the non-allergic composition.

The inventors surprisingly found in an internationally recognised model for allergy, that when prebiotic fibres are combined with probiotic bacteria (preferably Bifidobacteria) a synergistic effect was present on the prevention of allergic reactions. This synergistic effect is potentially very beneficial to the infants, but could also be beneficial to adults.

BRIEF DESCRIPTION OF DRAWINGS

FIG. 1 shows the allergic response for various compositions tested in accordance with an Internationally recognised mouse vaccine model.

FIG. 2 demonstrates the synergistic effect of TD1 (*Bifidobacterium breve*) and dietary fibers (OS) in a mouse casein allergy model.

DETAILED DESCRIPTION OF THE INVENTION

A preferred embodiment according to the invention comprises the use of a composition comprising free amino acids as a sole source of protein, a fatty acid source comprising long chain polyunsaturated fatty acids, a carbohydrate source comprising digestible and indigestible carbohydrates, and milk protein free Bifidobacteria for the manufacture of a composition for treating a person suffering from a. colic, congestion, runny nose, wheezing, vomiting, diarrhea, bloody stools, mucus in stools, rash, eczema, gastroesophageal reflux, eosinophilic esophagitis or asthma;

b. cow's milk allergy and/or food protein intolerance; and/or c. infections, wherein the indigestible carbohydrate is selected from a milk protein free source and the total composition is essentially free of intact proteins.

The term "sole source of protein" as herein means that present composition (preferably) contains at least 99 wt. % amino acids based on total protein, preferably at least 99.5, more preferably at least 99.9 wt. %.

The invention further provides composition comprising a protein component, a fat component, a digestible carbohydrate component, a non-digestible carbohydrate and bifidobacteria wherein;

a) the protein component contains more than 99 wt. % free amino acids based on total protein, and comprising at least the following free amino acids: alanine, arginine, aspartic acid, cysteine, glycine, histidine, isoleucine, leucine, lysine, methionine, proline, serine, threonine, tryptophan, tyrosine, valine and glutamine;
b) the digestible carbohydrate component contain less that 2 wt. % lactose based on total digestible carbohydrate;
c) the non-digestible carbohydrate comprises soluble fructan with an average DP between 2 to 200 and a soluble galacturonic acid with an average DP between 2 and 200; and
d) the fat component comprises between 0.1 and 5 wt % LCPUFA based on total fatty acid content.

As is shown in FIG. 1, the combination of long chain soluble fructans (LFOS) with an acid oligosaccharide (AOS), which was in this case pectin hydrolysate, work as well as the bifidobacteria when tested in the mouse model. It is clear however that if the oligosaccharides are combined with the Bifidobacteria the effects are strongly improved.

In a preferred embodiment the nutritional composition comprises both the non digestible fibres and the Bifidobacteria since this composition gives the best results in the allergic mouse model. (see FIG. 1). Preferably *Bifidobacterium breve* is used.

Non-Digestible Carbohydrate

Fructans are fructose based neutral oligosaccharides (>50% of the monose units are fructose), preferably inulin, fructan and/or fructooligosaccharide, most preferably a mixture of long chain fructooligosaccharide (IcFOS) with an average DP between 10-60 and short chain fructooligosaccharide (scFOS) with an average DP between 3 and 10. Preferred embodiment comprises a mixture of IcFOS and scFOS in a ratio of 1:9 since this ratio comes closer to the composition of oligosaccharides in breast milk and has been proven to effectively stimulate the growth of bifidobacteria in infants.

The present method preferably comprises the administration of a serving comprising between 0.05 and 25 grams non-digestible saccharide, preferably between 0.1 and 5 grams. The present method preferably comprises the administration of a serving comprising between 0.05 and 25 grams scFOS, preferably between 0.1 and 5 gram scFOS. The present method preferably comprises the administration of 0.05 to 25 grams non-digestible saccharide per day, preferably between 0.1 and 5 grams per day.

Pectin Degradation Product

Pectin is divided into two main categories: high methoxylated pectin, which is characterized by a degree of methoxylation above 50% and low methoxylated pectin having a degree of methoxylation below 50%. As used herein, "degree of methoxylation" (also referred to as DE or "degree of esterification") is intended to mean the extent to which free carboxylic acid groups contained in the polygalacturonic acid chain have been esterified (e.g. by methylation). The present pectin is preferably prepared from high methoxylated pectin.

The pectin is preferably characterized by a degree of methoxylation above 20%, preferably above 30% even more preferably above 50%.

The pectin as used in the present method has an average degree of polymerization (DP) between 2 and 500, preferably between 10 and 250 and most preferably between 20 and 50. When a mixture of pectin's with different degrees of polymerization is used, the average DP of the acid oligosaccharide mixture is preferably between 3 and 1000, more preferably between 3 and 250, even more preferably between 3 and 50. It was found that a lower DP of the oligosaccharides improves the palatability and results in a reduced viscosity product if the acid oligosaccharide is administered in liquid form.

The pectin is preferably administered in an amount of between 0.1 and 100 gram per day, preferably between 0.4 and 50 grams per day, even more preferably between 1 and 20 gram per day.

A preferred embodiment comprises fructans and pectin degradation products in a ratio 50:50-95:5. Preferably the ratio is 85:15 since this is the ratio of neutral oligosaccharides and acidic oligosaccharides as present in mother's milk.

Probiotic Bacteria

The probiotic bacteria that are suitable for use in the invention should preferably have at least a positive effect in the mouse allergy model as described in the examples below. The probiotics further must be harvested in substantial absence of food allergens. This requires special procedures or culture media without intact proteins for the preparation of the probiotic bacteria.

Preferred embodiment therefore comprises probiotic bacteria in substantial absence of intact food proteins or food allergens, specifically in substantial absence of milk proteins.

In a preferred embodiment the probiotic bacteria are bifidobacteria. Even more preferred the probiotic bacterium is *Bifidobacterium breve*. Bifidobacteria have the strongest tolerance inducing effect in the mouse models used and are therefore preferred. In particular *Bifidobacterium breve* is highly effective.

In another preferred embodiment the Bifidobacteria are non-viable. This has the advantage that the shelf life of the product becomes longer and that the immune modulatory activity of the bacteria becomes independent of the number of live bifidobacteria. Experiments have shown that immune stimulatory effects of non-viable bacteria is similar and sometimes even better than the activity of live bifidobacteria.

The present composition preferably comprises $10^2$ to $10^{13}$ colony forming units (cfu) of bifidobacteria per gram dry weight of the present composition, preferably $10^2$ to $10^{12}$ cfu, more preferably $10^5$ to $10^{10}$ cfu, most preferably from $10^4$ to $5 \times 10^9$ cfu.

Amino Acids

Amino acids can be used in nutritional formula for babies and infants. However, the composition of the amino acids in the formula preferably comprises all essential amino acids except for patients with phenylketonuria (PKU) and non-PKU inborn errors of metabolism, and is preferably optimal for baby food or infant nutrition. The inventors than found that the most optimal amino acid composition should be as close as possible to the amino acid composition of the protein fraction of mothers' milk. This results in a preferred amino acid composition as depicted in table 1 (see infra).

In a preferred embodiment the composition comprises less than 1 wt. % peptides based on total protein and more than 99 wt. % free amino acids based on total protein, comprising at least the following free amino acids: alanine, arginine, aspartic acid, cysteine, glycine, histidine, isoleucine, leucine, lysine, methionine, proline, serine, threonine, tryptophan, tyrosine, valine and glutamine;

Formula

Formula according to the invention comprise free amino acids as nitrogen source, fat including a fat blend comprising LCPUFA and carbohydrates. Vitamins and minerals are added according to legislation requirements.

The present composition preferably provides nutrition to the infant, and comprises a lipid component, a protein component and a carbohydrate component. The lipid component preferably provides 5 to 50% of the total calories, the protein component preferably provides 5 to 50% of the total calories, and the carbohydrate component preferably provides 15 to 90% of the total calories. The present composition is preferably used as an infant formula, wherein the lipid component provides 35 to 50% of the total calories, the protein component provides 7.5 to 12.5% of the total calories, and the carbohydrate component provides 40 to 55% of the total calories. For calculation of the % of total calories for the protein component, the total of energy provided by the amino acids needs to be taken.

LCPUFA

The content of LC-PUFA with 20 and 22 carbon atoms in the present composition, preferably does not exceed 15 wt. % of the total fat content, preferably does not exceed 10 wt. %, even more preferably does not exceed 5 wt. % of the total fat content. Preferably the present composition comprises at least 0.1 wt. %, preferably at least 0.25 wt, more preferably at least 0.5 wt. %, even more preferably at least 0.75 wt. % LC-PUFA with 20 and 22 carbon atoms of the total fat content. The Docosahexaenoic acid (DHA) content preferably does not exceed 5 wt. %, more preferably does not exceed 1 wt. %, but is at least 0.1 wt % of the total fat. As arachidonic acid (AA) was found to be particularly effective in reducing tight junction permeability, the present composition comprises relatively high amounts, preferably at least 0.1 wt. %, even more preferably at least 0.25 wt. %, most preferably at least 0.5 wt. % of the total fat. The AA content preferably does not exceed 5 wt. %, more preferably does not exceed 1 wt. % of the total fat. Excess metabolites from AA may cause inflammation. Hence, the present composition preferably comprises AA and DHA, wherein the weight ratio AA/DHA preferably is above 0.25, preferably above 0.5, even more preferably above 1. The ratio is preferably below 25.

The LC-PUFAs are preferably non-fish derived single cell oils, e.g. available from Martek.

Preferred features for compositions in accordance with the invention are set out in Tables 1-3.

TABLE 1

Amino acid content of composition according to the invention

| | | AA content as percentage of total AA | | | |
|---|---|---|---|---|---|
| | | Range (g/100 g) | | | |
| Amino Acid | Units | Infant 0-1 year | | Infant 1-10 year | |
| Ala | gm | 3.95 | 4.01 | 3.12 | 3.03 |
| Arg | gm | 6.99 | 7.02 | 14.24 | 13.91 |
| Asp | gm | 6.54 | 6.57 | 5.73 | 5.59 |
| Cys | gm | 2.59 | 2.58 | 1.85 | 2.91 |
| Glu acid | gm | | 0.00 | 0.00 | 0.00 |
| Gly | gm | 6.15 | 6.12 | 5.11 | 5.01 |
| His | gm | 4.02 | 3.99 | 3.71 | 3.61 |
| Iso | gm | 6.15 | 6.12 | 5.11 | 5.01 |
| Leu | gm | 10.56 | 10.51 | 8.54 | 8.32 |
| Lys | gm | 7.19 | 7.19 | 6.25 | 6.11 |
| Meth | gm | 1.68 | 1.69 | 4.02 | 3.90 |
| Phe | gm | 7.51 | 7.47 | 7.10 | 6.93 |
| Pro | gm | 4.73 | 4.72 | 5.97 | 5.82 |
| Ser | gm | 4.60 | 4.61 | 3.71 | 3.61 |
| thr | gm | 5.18 | 5.17 | 4.29 | 4.19 |
| Try | gm | 2.07 | 2.08 | 1.72 | 1.69 |
| tyr | gm | 4.73 | 4.72 | 1.44 | 1.40 |
| Val | gm | 6.74 | 6.74 | 5.42 | 5.30 |
| Car | gm | 0.06 | 0.06 | 0.10 | 0.12 |
| tau | gm | 0.19 | 0.20 | 0.17 | 0.17 |
| Glu | gm | 8.42 | 8.43 | 12.35 | 13.39 |
| total | gm | 100 | 100 | 99.97 | 100 |

TABLE 2

Nutritional infant formula for allergic infants
Nutritional Profile of formula for infants
according to the invention (powder)

| | Units | Level/100 g | Level/100 kcal |
|---|---|---|---|
| Protein Equivalent | gm | 13 | 2.9 |
| Energy | kcals | 455 | 100 |
| Nitrogen | gm | 2.1 | |
| Carbohydrate | gm | 49 | 10.8 |
| Fat (total) | gm | 23 | 5.1 |
| (MCT) | % | 33 | |
| (LCT) | % | 67 | |

TABLE 3

Ranges in Long Chain Polyunsaturated
(LCP) fatty acid composition

| | % Fatty acids | | |
|---|---|---|---|
| | Preferred | Range +/− 25% | |
| Arachidonic acid | 0.35 | 0.26 | 0.44 |
| Docosahexanoic acid | 0.20 | 0.15 | 0.25 |
| Total LCP | 0.55 | 0.41 | 0.69 |

The preferred ranges in the oligosaccharide composition are 0.4-1.2 g/100 ml wherein 85 w % is scFOS and lcFOS and 15 w % is pectin hydrolysate. Preferably the ratio scFOS to lcFOS is between 2 and 20 even more preferably the ratio is 9.

One preferred embodiment of milk protein and allergen free, nutritionally complete powdered formulation in accordance with the invention which is suitable for dilution with water to form an enteral feed comprises:

| Component | Per 100 g Powder |
|---|---|
| Protein equivalent (g) | 13 |
| Total amino acids (g) | 15.5 |
| Total fat (g) | 23 |
| Sunflower oil (g) | 4 |
| Fractionated coconut oil (g) | 7 |
| Canola oil (g) | 4 |
| High oleic sunflower oil (g) | 6.6 |
| ARASCO ™ oil (g) | 0.21 |
| DHASCO ™ oil (g) | 0.11 |
| Carbohydrate: Maltodextrin (g) | 49 |
| Prebiotic (g) | 5.33 |
| ScFOS (g) | 4.1 |
| lcFOS (g) | 0.43 |
| AOS (g) | 0.8 |
| Probiotic: B Breve (colony forming units; CFU) | $1 \times 10^{10}$ |
| Other vitamins/minerals/trace elements | Balance |

The above formulation provides approximately 455 kcal of energy per 100 g powder.

The formulation may be diluted with cooled, boiled water to provide a recommended concentration of 15% w/v.

Uses

Preferable the composition is used for treating an infant (particularly with an atopic constitution) suffering from
  a. colic, congestion, runny nose, wheezing, vomiting, diarrhea, bloody stools, mucus in stools, rash, eczema, gastroesophageal reflux, eosinophilic esophagitis or asthma;
  b. cow's milk allergy and/or food protein intolerance; and/or
  c. infections The composition can also preferably be used to improve the stool characteristics of infants suffering from the above mentioned symptoms. The composition is specifically designed for infants between 0- and 3 years. With some adaptations in the amino acid profile (see table 1) the composition is also suitable for infants between 3 and 10 years old. Allergic infants often suffer from diarrhea but constipation also occurs. A preferred composition can be used to prevent and treat these symptoms comprises fibres according to the composition of mothers milk, wherein the ratio scFOS/lcFOS is 9:1 and additionally pectin hydrolysate is present.

EXAMPLES

In order to determine the immune stimulating effects of oligosaccharides and probiotic *Bifidobacterium breve* (TD1) tests were performed in an internationally recognized mouse vaccine model (FIG. 1) and in an allergy model (FIG. 2).

Materials and Method of the Vaccine Model

Mice

Female 6- and 8-week old C57Bl/6JOIaHsd mice were obtained from Harlan (Horst, the Netherlands) and kept under normal conditions with a 12 h dark and light cycle and free access to food and water. All experiments were approved by an independent animal experiments committee (DEC Consult, Bilthoven, The Netherlands).

Diets and Oligosaccharide Preparations

All animals received semi-purified AIN-93G-based diets (Research Diet Services, Wijk bij Duurstede, The Netherlands). All supplemented oligosaccharide products were exchanged for the same amount of total carbohydrates, to keep this parameter equal. In addition, this approach resulted in a comparable overall carbohydrate composition in different diets, to ensure that the gut flora was minimally influenced by differences between control and test diets in parameters such as gut passage time and fluid retention. The oligosaccharides were mixed into the AIN-93G diet and pressed into pellets.

Vaccination Protocol and DTH Response

Vaccination experiments were performed using Influvac (Solvay Pharmaceuticals, Weesp, the Netherlands) from season 2002/2003. It is an inactivated influenza virus vaccine based on isolated haemagglutinin (HA) and neuraminidase antigens of three strains of myxovirus influenza, in a dose equivalent to 30 μg/mL HA per strain (90 μg/mL HA in total). An oil-adjuvant was used in all vaccinations (Stimune, previously known as Specol; Cedi-diagnostics, Lelystad, The Netherlands). The mice received a primary vaccination and a booster vaccination, consisting of a subcutaneous (sc) injection of a 1:1 mix of vaccine and adjuvant in a total volume of 100 μL. The booster vaccination was given 21 days after the primary vaccination. The experiments ended 10 days after booster vaccination. Blood samples (taken by retro-orbital puncture) were taken before primary and secondary vaccination and at the end of the experiment. Negative control groups that were included in all experiments (indicated with 'sham group') received injections with a 1:1 mix of PBS and adjuvant in a total volume of 100 μL. Sham groups were never used for statistical comparisons to supplemented groups, but served solely to demonstrate the specificity of vaccine-induced responses. DTH reactions were induced 9 days after booster vaccination, by sc injection of 25 μL Influvac into the ear pinnae of both ears. Ear thickness was measured in duplicate before vaccine challenge and 24 h thereafter, using a digital micrometer (Mitutoyo Digimatic 293561, Veenendaal, The Netherlands). The DTH response was calculated by subtracting the basal ear thickness from the value at 24 h after challenge.

Material and Methods of the Cows Milk Protein Allergy Model

Chemicals

Casein and whey are obtained from DMV international, Veghel, The Netherlands. Cholera toxin is purchased from Quadratech Diagnostics, Epsom, UK. PBS is purchased from Cambrex Bio Science, Verviers, Belgium. Elisa coating buffer is obtained from Sigma, Alphen aan den Rijn, The Netherlands. Biotin labeled rat anti mouse IgE is purchased from BD Biosciences, Alphen aan den Rijn, The Netherlands. All other chemicals are obtained from Sigma-Aldrich-Chemie, Zwijndrecht, The Netherlands.

Oral Sensitization and Challenge of Mice

Three- to 5-week-old specific pathogen free female C3H/HeOuJ mice (n=4-6 per group) were purchased from Charles River Laboratories (Maastricht, the Netherlands), maintained on cow's milk protein free mouse chow (Special Diets Services, Witham, Essex, UK) and housed in the animal facility at Utrecht University. Animal care and use were performed in accordance with the guidelines of the Dutch Committee of Animal Experiments. Mice were intra gastric (i.g.) sensitized with 0.5 mL homogenized casein (40 mg/mL PBS) with cholera toxin (CT, 20 μL/mL PBS) as an adjuvant using a blunt needle. Control mice received CT alone or PBS. Mice were boosted weekly for a period of 6 weeks, one week after the last sensitization mice were challenged i.g. with 100 mg casein.

Blood samples were collected and centrifuged thereafter (15 min. at 13500 rpm.). Sera were stored at −70° C. Mice were sacrificed by cervical dislocation half an hour after i.g. challenge.

Allergen Specific Skin Response

The acute allergen specific skin response was measured after injection of the specific protein in the ear pinnae. Before i.g. challenge (t=0), the control, casein sensitized mice were injected intra dermal (i.d.) in the left ear with 20 μL homogenized casein (0.5 mg/mL in PBS) respectively. In the right ear 20 μL PBS was injected as a vehicle control. Also the CT and PBS mice received a casein ear challenge using PBS injections as control. Ear thickness was measured in duplicate using a digital micrometer (Mitutoyo, Veenendaal, The Netherlands), at 0, 1, 4 and 24 hour after challenge. The allergen specific ear swelling was calculated by subtracting the basal (0 h) and the control (right ear) thickness from the value measured at the three different time points (1, 4 and 24 h).

Measurement of Serum Immunoglobulin and Mouse Mast Cell Protease-1 Levels

Concentrations of total IgE and levels casein or whey specific IgE, IgG1 and IgG2a were determined in serum of sacrificed mice by means of ELISA. Microlon plates (Greiner, Alphen aan den Rijn, The Netherlands) were coated with casein in coating buffer or rat anti-mouse IgE (1 μg/mL) in PBS for 18 hours at 4° C. Plates were washed and blocked for 1 hour with 5% BSA. Serum samples were applied in several dilutions and incubated for 2 hours at room temperature. Plates were washed 5 times and incubated with 1 μg biotin labeled rat anti mouse IgE for one and a half hour at room temperature. After washing plates were incubated with horse radish peroxidase (HRP) for one hour, washed and developed with o-phenylendiamine (OPD). The reaction was stopped with 4M $H_2SO_4$ and absorbance was measured at 490 nm on a Benchmark microplate reader (Biorad, California, USA). Serum concentrations of mouse mast cell protease-1 (mMCP- 1) were determined as described previously using a commercially available ELISA kit (Moredun Scientific Ltd., Midlothian, UK).

The results of the mouse vaccine model are shown in FIG. 1 from which it is clear that the combination of TD1 (=*Bifidobacterium breve*) provides the strongest effect on DTH response and is significantly better than TD1 alone or any other combination tested.

The results of the mouse casein allergy model are shown in FIG. 2 and demonstrates that the combination of dietary fiber and TD1 synergistically inhibits the "allergenic" DTH response to casein.

The invention claimed is:

1. A method of treating a person suffering from eosinophilic esophagitis, asthma or cow's milk allergy comprising administering to said person a milk protein-free composition comprising effective amounts of:
   (a) a protein-free portion consisting of:
      (i) free amino acids as the sole source of amino acids in the protein-free portion, wherein the free amino acids comprise at least alanine, arginine, aspartic acid, cysteine, glycine, histidine, isoleucine, leucine, lysine, methionine, proline, serine, threonine, tryptophan, tyrosine, valine, and glutamine,
      (ii) fatty acids comprising long-chain polyunsaturated fatty acids (LCPUFA),
      (iii) digestible carbohydrates, and
      (iv) indigestible carbohydrates obtained from a milk protein-free source; and
   (b) Bifidobacteria obtained from a milk-protein-free culture;
wherein the milk protein-free composition is free of protein fragments of milk, and other than (b) is essentially free of intact proteins.

2. The method according to claim 1 wherein the person is an infant in the age between 0 and 36 months.

3. A method of stimulating the maturation of the immune system in an infant with an atopic constitution, comprising administering to said infant a milk protein-free composition comprising effective amounts of:
   (a) a protein-free portion consisting of:
      (i) free amino acids as the sole source of amino acids in the protein-free portion, wherein the free amino acids comprise at least alanine, arginine, aspartic acid, cysteine, glycine, histidine, isoleucine, leucine, lysine, methionine, proline, serine, threonine, tryptophan, tyrosine, valine, and glutamine,
      (ii) fatty acids comprising long-chain polyunsaturated fatty acids (LCPUFA),
      (iii) a digestible carbohydrate, and
      (iv) an indigestible carbohydrate obtained from a milk protein-free source; and
   (b) Bifidobacteria obtained from a milk-protein-free culture;
wherein the milk protein-free composition is free of protein fragments of milk, and other than (b) is essentially free of intact proteins.

4. The method according to claim 1 wherein the composition comprises by en % thereof between 5 en % and 16 en % said amino acids; between 30 en % and 60 en % said fatty acids, having between 0.1 en % and 5 en % said LCPUFA; and between 25 en % and 75 en % said digestible carbohydrate.

5. The method according to claim 4 wherein the composition comprises between 0.2 en % and 1 en % said LCPUFA.

6. The method according to claim 1 wherein the indigestible carbohydrates obtained from a milk protein-free source comprises (i) soluble fructan with an average degree of polymerisation between 3 to 200 and (ii) a soluble galacturonic acid with an average degree of polymerisation between 3 and 200.

7. The method according to claim 3 wherein the composition comprises by en % thereof between 5 en % and 16 en % said amino acids; between 30 en % and 60 en % said fatty acids, having between 0.1 en % and 5 en % said LCPUFA; and between 25 en % and 75 en % said digestible carbohydrate.

8. The method according to claim 7 wherein the composition comprises between 0.2 en % and 1 en % said LCPUFA.

9. The method according to claim 3 wherein the indigestible carbohydrate obtained from a milk protein-free source comprises (i) soluble fructan with an average degree of polymerisation between 3 to 200 and (ii) a soluble galacturonic acid with an average degree of polymerisation between 3 and 200.

10. A method of treating a person suffering from an atopic condition, comprising administering to said person a milk protein-free composition comprising effective amounts of:
   (a) a protein-free portion consisting of:
      (i) free amino acids as the sole source of amino acids in the protein-free portion, wherein the free amino acids comprise at least alanine, arginine, aspartic acid, cysteine, glycine, histidine, isoleucine, leucine, lysine, methionine, proline, serine, threonine, tryptophan, tyrosine, valine, and glutamine,
      (ii) fatty acids comprising long-chain polyunsaturated fatty acids (LCPUFA),
      (iii) a digestible carbohydrate, and
      (iv) an indigestible carbohydrate obtained from a milk protein-free source; and
   (b) Bifidobacteria obtained from a milk-protein-free culture;
wherein the milk protein-free composition is free of protein fragments of milk, and other than (b) is essentially free of intact proteins.

* * * * *